United States Patent
Miethke

(10) Patent No.: US 6,926,691 B2
(45) Date of Patent: Aug. 9, 2005

(54) HYDROCEPHALUS VALVE

(76) Inventor: Christoph Miethke, Verdistrasse 4, Bergholz-Rehbruecke (DE), D-14558

(*) Notice: Subject to any disclaimer, the term of this patent is extended or adjusted under 35 U.S.C. 154(b) by 0 days.

(21) Appl. No.: 10/458,755

(22) Filed: Jun. 9, 2003

(65) Prior Publication Data
US 2004/0024346 A1 Feb. 5, 2004

Related U.S. Application Data

(63) Continuation of application No. PCT/EP01/14585, filed on Dec. 11, 2001.

(30) Foreign Application Priority Data

Dec. 11, 2000 (DE) .......................... 100 61 611
Feb. 3, 2001 (DE) .......................... 101 05 315

(51) Int. Cl.⁷ ............................................. A61M 5/00
(52) U.S. Cl. ............................................. 604/9; 604/8
(58) Field of Search ............................ 604/8–10, 247, 604/6.1, 523, 264, 265; 600/561, 300

(56) References Cited

U.S. PATENT DOCUMENTS

| 4,106,510 A | 8/1978 | Hakim et al. |
| 4,261,341 A | 4/1981 | Hakim et al. |
| 4,443,214 A | 4/1984 | Marion |
| 4,551,128 A | 11/1985 | Hakim et al. |
| 4,595,390 A * | 6/1986 | Hakim et al. ............ 604/9 |
| 4,605,395 A | 8/1986 | Rose et al. |
| 4,610,658 A * | 9/1986 | Buchwald et al. ......... 604/9 |
| 4,627,832 A | 12/1986 | Hooven et al. |
| 4,772,257 A | 9/1988 | Hakim et al. |
| 4,776,838 A | 10/1988 | Sainte-Rose et al. |
| 5,069,663 A | 12/1991 | Sussman |
| 5,291,899 A * | 3/1994 | Watanabe et al. ........ 600/561 |
| 5,368,556 A | 11/1994 | Lecuyer |
| 5,643,195 A * | 7/1997 | Drevet et al. ............ 604/9 |
| 5,800,376 A | 9/1998 | Watson et al. |
| 5,843,013 A | 12/1998 | Lecuyer |
| 5,928,182 A | 7/1999 | Kraus et al. |
| 5,980,480 A | 11/1999 | Rubenstein et al. |
| 6,022,333 A | 2/2000 | Kensey |
| 6,336,924 B1 | 1/2002 | Lecuyer et al. |
| 6,585,677 B2 * | 7/2003 | Cowan et al. ............ 604/9 |
| 6,684,904 B2 * | 2/2004 | Ito ........................ 137/530 |

FOREIGN PATENT DOCUMENTS

| DE | 27 52 087 | 8/1978 |
| DE | 30 20 991 | 12/1980 |
| DE | 40 26 202 | 2/1992 |
| DE | 43 07 387 | 9/1994 |
| DE | 44 01 422 | 7/1995 |
| DE | 195 35 637 | 3/1997 |
| DE | 196 54 990 | 6/1998 |
| DE | 199 15 558 | 10/2000 |
| EP | 0 060 369 | 9/1982 |
| EP | 0 115 973 | 8/1984 |
| EP | 0 135 991 | 4/1985 |

(Continued)

OTHER PUBLICATIONS

Leonhardt, S. u.s., "Ein computergestützter Prüfstand Für Liquor–Drainagesysteme" A Computer–aided Test Rig for CSF shunts, in. Biomedizinische Technik Bd. 39, Heft Jul. 8, 1994, pp. 188 to 195.

Miethke, Chr., Affeld K., "A New Valve for the Treatment of Hydrocephalus" in: biomedizinische Technik Bd. 39, Heft Jul. 8, 1994, pp. 184 to 187.

Primary Examiner—Angela D. Sykes
Assistant Examiner—Leslie Deak
(74) Attorney, Agent, or Firm—Lipsitz & McAllister, LLC

(57) ABSTRACT

In order to allow improved adaptation to the situation existing in a patient in the case of a hydrocephalus valve with an electric actuating system comprising a control system opening and closing the hydrocephalus valve, it is proposed that the control system is a time control system.

18 Claims, 3 Drawing Sheets

FOREIGN PATENT DOCUMENTS

| | | |
|---|---|---|
| EP | 0 421 557 | 4/1991 |
| EP | 94 103 011 | 3/1994 |
| EP | 0 617 975 | 10/1994 |
| EP | 0 670 740 | 9/1995 |
| EP | 0 798 012 | 10/1997 |
| FR | 2 772 278 | 6/1999 |
| GB | 2 143 008 | 1/1985 |

* cited by examiner

HYDROCEPHALUS VALVE

This application is a continuation of international application No. PCT/EP01/14585 filed on Dec. 11, 2001.

The present disclosure relates to the subject matter disclosed in international application PCT/EP 01/14585 of Dec. 11, 2001, which is incorporated herein by reference in its entirety and for all purposes.

BACKGROUND OF THE INVENTION

The invention relates to a hydrocephalus valve with an electrical actuating system, comprising a control system opening and closing the hydrocephalus valve.

In the case of people suffering from hydrocephalus there is the problem that raised internal pressure of the brain occurring because of excessive cerebrospinal fluid leads to serious problems for the people affected. The brain tissue is therefore damaged and permanently weakened and there are various symptoms such as dizziness, walking difficulty, headaches, nausea, sickness and dementia. Untreated, the disease can ultimately lead to the death of the patient. The type and extent of the symptoms occurring depend on the causes underlying the disease, general constitution, but primarily the age of the patient. In babies, the rise in pressure brings about an unnatural growth of the head; in adults, the substance of the brain is lost in favour of the water content in the interior of the skull.

There has only been a successful possibility for treating people suffering from hydrocephalus for about 50 years. For this an artificial drainage device is implanted which allows the drainage of the cerebrospinal fluid into other body regions in which the fluid which has been discharged, can then be broken down. Control of the drainage is undertaken here by valves which are intended to ensure the required pressure in the interior of the head. Since then a large number of diverse technical solutions have been proposed which extend the treatment possibilities or else are intended to hinder or restrict frequently occurring complications.

Until now three different types of valves were able to dominate the market:
1. Valve systems with a simple, rigid differential pressure valve,
2. Valve systems with a post-operative, percutaneously adjustable valve system and
3. Hydrostatic valve systems.

The rigid differential pressure valve of Group 1 is marketed as a sphere-cone construction (U.S. Pat. No. 5,069,663, DE 3020991) as a silicon slot valve or as a diaphragm valve. The valves are distinguished in that their opening behaviour is oriented to the lying position of the patient. In the standing position, such valves lead systematically to unphysiologically low, negative pressure in the head of the patient, which can lead to serious complications.

Representatives of the second group of valves introduce an improvement in that these valves operate like those of Group 1 but allow percutaneous adjustment of the opening characteristics, (U.S. Pat. No. 4,772,257, EP 0 421 557 A2, U.S. Pat. No. 5.928.182, EP 135 991 A1, GB 2143008 A, U.S. Pat. No. 4,551,128, EP 0 060 369). Therefore individual adaptation of the valve function to the individual patients is possible. Nevertheless, these valves do not eliminate the difficulty, either, that the physical conditions in the drainage system of the patient change as a function of posture. If the valves are adjusted to a low opening pressure, this will, on the one hand, favour the clinical outcome, but, on the other hand, simultaneously dramatically increase the danger of over-drainage in the standing position. Conversely, although adjustment to a very high value can reduce the danger of overdrainage, the clinical outcome to be achieved is thus simultaneously lastingly impaired, as the now available opening pressure for the lying position is significantly too high. Valves of Group 3 provide assistance here. Hydrostatic valves are distinguished in that they take into account the changing physical conditions in the drainage system of the patient with the aim of avoiding the problems described above as a result of over-drainage. Three different principles are exploited here.

The oldest construction was produced in the so-called anti-siphon device. According to the same principle, a plurality of different constructions were on the market up to now (EP 0 670 740 B1, U.S. Pat. No. 5,800,376, DE 2752087). Here the effect of the negative pressure at the outlet of the valve is systematically reduced to a minimum. However, opposing this advantage is the serious drawback that the subcutaneous pressure around the valve housing has a considerable influence on the mode of operation of the valve. Owing to tissue growth or an unfavourable position of the patient, this pressure may vary by considerable values and therefore even lead to absolute valve closure. In comparison to conventional valves, these valves have not proved superior, either (Drake, Toronto).

The same is true for the second principle of the third group, the principle of so-called flow control. In flow-regulating valves it is to be ensured that the draining quantity is kept constant independently of the differential pressure at the valve. Whereas in conventional valves the drainage quantity increases proportionally to the differential pressure available, in flow-regulating valves this is impeded (Siphonguard [Codman], Orbis Sigma Valve [Cordis], Diamond Valve [Phoenix]; EP 798 012 A1, U.S. Pat. No. 4,627,832, U.S. Pat. No. 4,776,838). On average the natural liquor production is 23 ml/h. Flow-regulating systems specifically have the following problems.
1. It is technically impossible to ensure the value for the allowed drainage rate. Variances in the course of the production process remain too high (Aschoff, Schoener).
2. The natural variance of the production remains systematically disregarded. If the individual values are too high or too low this can lead both to overdrainage and to under-drainage.
3. The flow regulation is controlled via extremely small cross-sections on the opening mechanism. Particles in the liquor such as, for example cellular constituents have a dramatic influence on function and can easily clog the valve. International comparative studies have shown that this principle was not able to improve the treatment outcomes of hydrocephalus (Drake et al).

In contrast thereto significant improvements were determined after the introduction of gravitation-assisted valves (Meier, Sprung, Kiefer). Two different technical solutions are available on the market. The first approach produces flow control by the gravity-controlled switching over of two valves arranged in parallel (DE 4401422, DE 4307387, EP 94103011). This construction therefore adjusts two different pressure situations in the ventricle system of the patient as a function of his posture. In the second approach, the weight of spheres is exploited to adjust an opening pressure which is changeable as a function of position (EP 0 617 975, EP 0 115 973, DE 19535637). Although many problems could be solved by valve systems of this type the following aspects also remain unsolved here:
1. Adaptation of the valve characteristics to growth or age-related changes or other changes of physiological boundary conditions is not possible.

2. A deliberate, non-invasive adjustment of the valve properties with different adjustments for different body positions of the patient is not possible.
3. Consistent treatment of patients right up to the drainage (which has perhaps become superfluous) being turned off, is not possible.
4. The appropriate adaptation of liquor drainage to individual particularities is not possible.
5. Valves remain a narrow point of discharge. Increase in the drainage reliability by providing wider opening ducts even in the valve seat would be desirable.
6. All previously offered solutions are based exclusively on the differential pressure principle. Other parameters which could also influence sensible control in liquor drainage, are not included. It would be conceivable, for example, to include muscle potentials or other electronic signals. Such signals cannot be taken into consideration in previously offered solutions.
7. Intelligent control, which evaluates as a function of the situation, of valve properties is impossible with previous solutions.
8. Subsequent analysis of incidents is not possible. The explanation for causes for occurrences often stay suppositions.

These problems can partly be overcome by solutions such as are described in DE 19915558 A1. An electronically controlled implant is proposed there which controls the brain pressure of hydrocephalus patients. However, the detection of pressure values in the patient is connected with great uncertainties, and therefore this method is not suitable for satisfactorily controlling the fluid drainage in the long term.

A similar system is described in DE 19654990 A1, in which the drainage quantity through the drainage system is controlled by electromagnetic control elements, for example the characteristics of a spring valve are adjusted, the size of a gap in the discharge, and similar. This necessitates an extraordinarily complicated construction of the valve, and moreover it must be assumed that the controlled variables, i.e. flow and pressure are constant over time and only have to be adjusted if necessary in the course of doctors' visits to then be valid for a longer time period.

SUMMARY OF THE INVENTION

The invention is based on the object of producing improved adaptation of the fluid drainage with a hydrocephalus valve which is reliably and simply constructed.

This object is achieved in a hydrocephalus valve of the type described at the outset according to the invention, in that the control system is a time control system.

Time control of this device keeps the hydrocephalus valve open over a specific time period and closes it over a specific time period, for example the valve may remain open for a long time at night during reliable lying phases and during the day the switch is only opened once an hour for 30 seconds or a few minutes.

It is particularly advantageous if the time control system is programmable, so that the opening durations and the closing durations can be changed by a programme of this type. It is possible, for example, to develop in this manner an individual time control programme for each patient which is tailored to his needs. It is also possible to provide a plurality of time programmes of this type for one and the same patient, so that for example in the sleeping phase a different time control programme is used than during the waking and standing phase. In particular it is possible for the doctor to change the drainage behaviour of the liquid at any time and adapt it to needs, by corresponding programming.

In the process this may be pure control; the time course is input directly by the programme and remains uninfluenced by the results achieved thereby.

In another preferred embodiment, however, it may be provided that the time control system can be influenced by signals from at least one measuring instrument.

These measuring instruments may, for example be a pressure measuring apparatus measuring pressure values in the brain, in the surroundings or at other interesting points, a position sensor, which determines whether the patient is lying, standing or moving, a measuring instrument for determining muscle potentials or brain current potentials etc. The influence leads here to a change in the time control programme, so changes occur in the open times and in the closed times.

It is favourable if there is associated with the time control system a data memory which detects all the opening and closing states over time and builds up reference material therewith, enabling checking at any time.

In a preferred embodiment it is provided that the hydrocephalus valve comprises a switching valve, which is to be adjusted by the electrical actuating system between an open position and a closed position. The opening behaviour, for example the closing force of a valve body or the size of a through-flow cross-section, is not influenced, rather there is only a switching over with an unchanged through-flow cross-section between the open position and closed position, so that it is ensured that no disturbance of the drainage behaviour occurs when the hydrocephalus valve is open owing to tissue parts in the fluid and other deposits.

It is particularly advantageous if the switching valve is stable in the open position and in the closed position when the electrical actuating system is not activated, as energy is only needed to switch over the switching valve, but not to maintain one of the two end positions of the switching valve.

In a preferred embodiment, it is provided that the switching valve has a spherical valve body, which rests in a sealing manner in the closed position on a valve aperture and in the open position rests in a recess laterally adjacent to the valve aperture. This produces a particularly simple construction for a switching valve of this type.

The actuating system may comprise a slide which on the one hand, displaces the valve body and, on the other hand, the valve aperture and the recess, relative to one another. The displacement here may, on the one hand, be a displacement of the valve body, but it is also possible that the valve aperture with the recess arranged next to it, is displaced relative to a stationary valve body.

The actuating system may comprise an electromagnetic drive, a piezoelectric drive or a current-carrying bimetal; still further drives which are common per se are also possible here.

In a further preferred embodiment, it is provided that the time control system changes the opening behaviour of a closing valve. This may be exclusively the case or else may also be for changing over between the open position and closed position. The opening behaviour may be changed, for example, by a change of cross-section, by changing spring forces etc.

BRIEF DESCRIPTION OF THE DRAWINGS

The following description of preferred embodiments of the invention is used in conjunction with the drawings for more detailed description. In the drawings.

DESCRIPTION OF THE PREFERRED EMBODIMENTS

Figure 1:
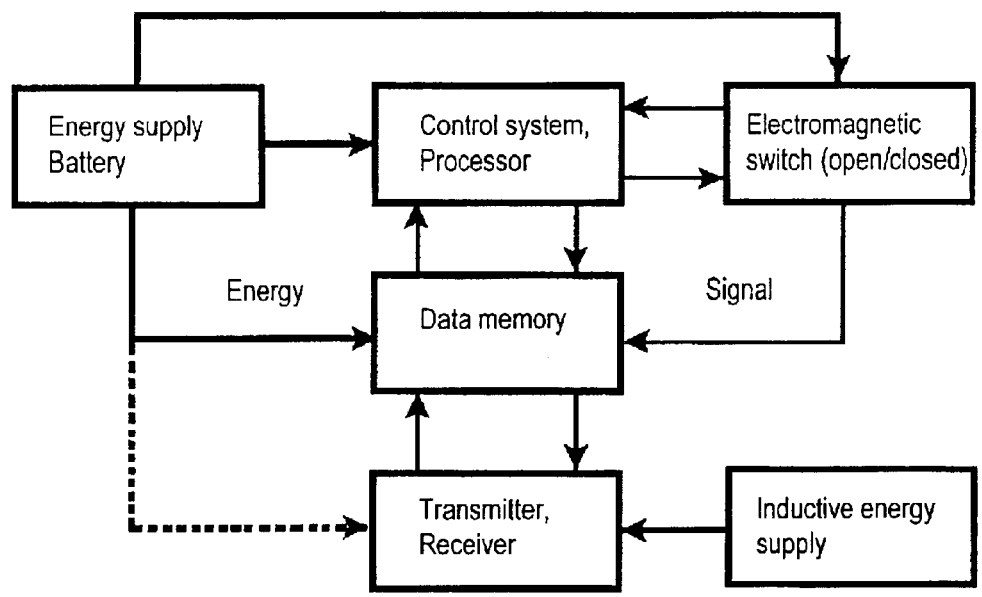
FIG. 1 shows a block diagram of a simple time control system for an electromagnetic switching valve.

The hydrocephalus valve system shown in the drawings comprises an energy unit (battery), a processor, a data memory, an electromagnetic switch, a transmitting and receiving unit and optionally a unit for inductive energy supply. FIG. 1 shows the block diagram for the mode of operation of the invention.

FIG. 1 shows the simplest mode of construction of a valve system. A time-dependent control signal s(t) is input into the data memory via the transmitter. The control signal s(t) contains control information which can be individually set up for each patient about the opening state of the electromagnetic switch at each point in time t. Thus, for example, the opening state at night can last longer than during the day. There is the possibility of setting up an individual profile according to the habits or needs of the patient. This opening profile can be adapted at any time to possible changes.

The data memory passes the information to the control unit which in turn controls the electromechanical components. The switch passes the information on its state (open or closed) to the processor and the data memory. The transmitting and receiving unit may preferably be activated by an inductive energy supply and be supplied with energy. The energy supply may also be via the battery.

Figure 2:
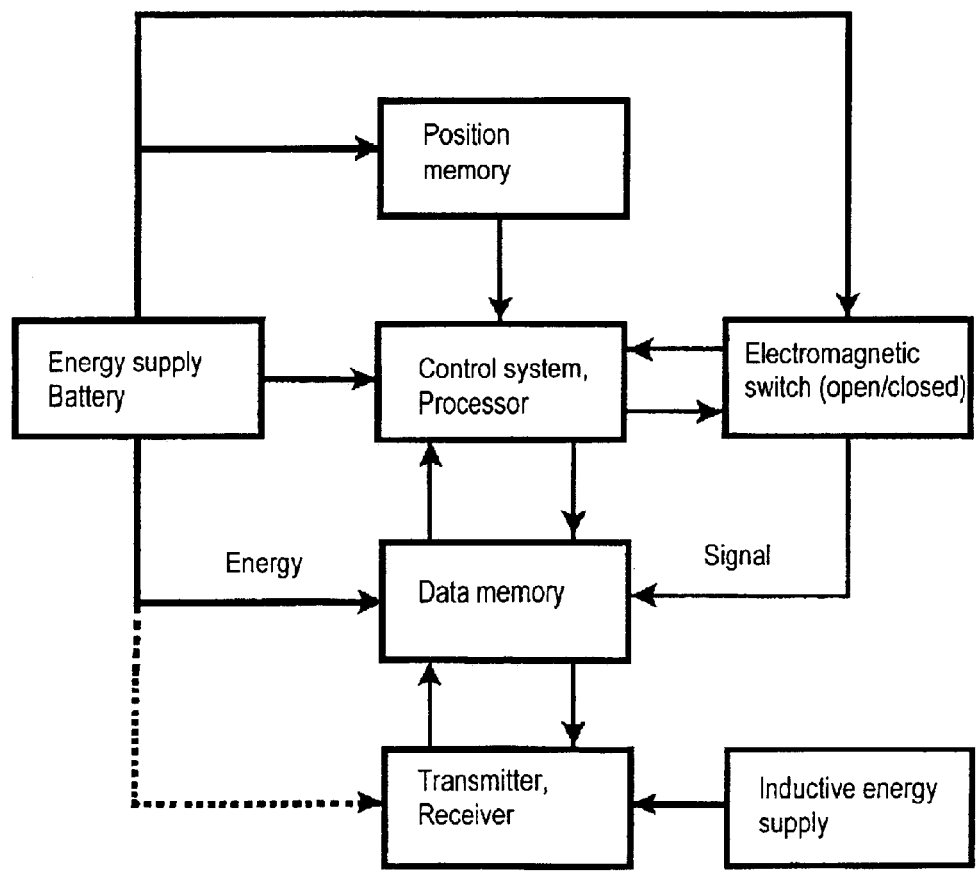
FIG. 2 shows a view similar to FIG. 1 in a time control system which can be influenced by the signals of a position sensor.

A more complex variation of the invention is shown in FIG. 2. Here, the unit shown in FIG. 1 is supplemented by a position sensor. This sensor passes the posture of the patient to the control unit, which charges the desired value of the valve actuation system according to the programming transmitted.

Figure 3:
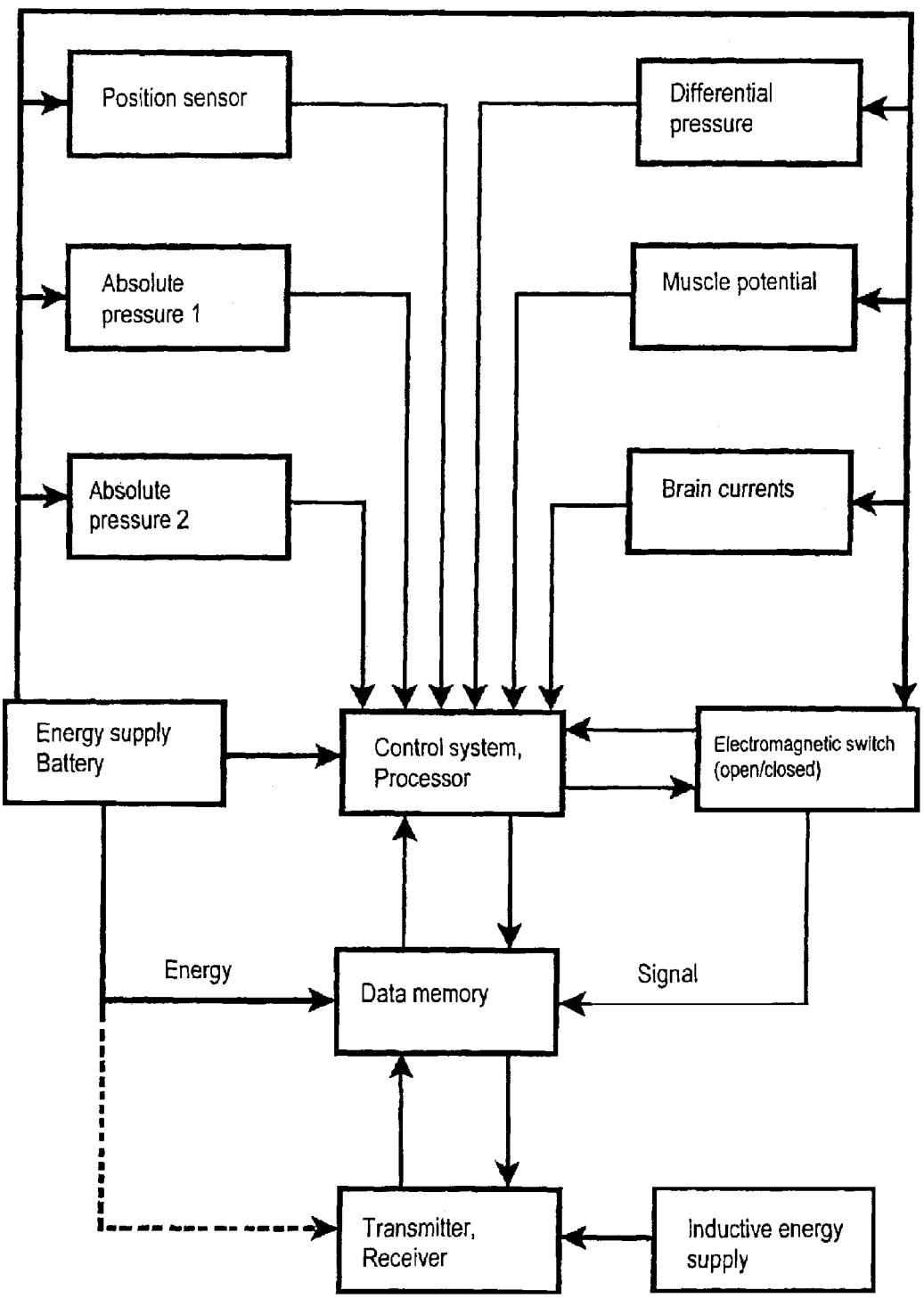
FIG. 3 shows a view similar to FIG. 2 with a time control system, which can be influenced by signals from a plurality of measuring devices.

Apart from the position sensor, further measuring devices determining characteristic values can be included in the determination of the desired value. Muscle potentials and pressure values taken can also be determined for this purpose. The inclusion and intelligent evaluation of measured pressure values can above all be used for optimising the drainage. However, the pressure values are not detected to establish a drainage controlled by the differential pressure at the valve as in conventional drainages. However, the pressure can be used for the purpose of detecting short-term changes and taking them into account accordingly. The problem of drift of pressure sensing devices thus becomes insignificant. The detection of the absolute pressure before and after the switch could provide reliable indications of the actual drainage situation. If, for example a patient stands up with the switch closed this leads, both above and below the switch to characteristic states, which can be controlled accordingly. The evaluation of states of this type can take place extracorporeally after transmission of the data picked up and can be used to set up improved control algorithms. The exclusive detection of differential pressure at the switch offers findings to optimise the control algorithm. FIG. 3 shows a block diagram for a complex embodiment of the invention of this type.

Figure 4:
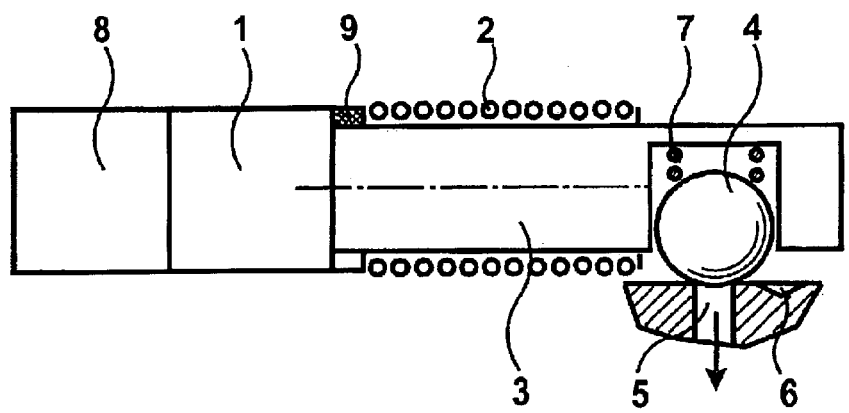
FIG. 4 shows a schematic longitudinal sectional view of a bi-stable switching valve and FIG. 5 shows a typical control profile for a time control system.

FIG. 4 shows an embodiment example of an electromechanical switch for opening and closing the drainage. An electronic system 1 is supplied with power by a battery 8. Depending on the switching direction a current is applied to a coil 2, so a magnetic field is generated which moves a slide 3. The slide 3 can adopt two different rest states, which are secured by a spring 7. The spring is selected in such a way that, on the one hand, the spring secures the seat of a sphere 4 even in the event of vibrations, but on the other hand the force to displace the sphere 4 remains small. Either, it rests in the aperture in a valve outlet 5 (position 1), or else in a blind hole 6 (position 2). The outlet hole on the valve outlet 5 typically has a diameter of about 1 mm, corresponding to the internal diameter of a typical drainage line. If the sphere 4 which is preferably produced from a hard and light material, for example aluminium oxide ceramic and which preferably has a diameter which is about three times greater than the hole of the valve outlet 5, is pushed into position 1, the drainage is closed. If the sphere 4 is pushed into position 2, the total cross-section of the hole is exposed. This maximum aperture minimises the danger of blockage at the switch. The position of the slide 3 can be continuously detected via a detector 9. The control of the slide 3 may take place both as a pure time control according to a predetermined individual patient-dependent time profile or else may also be calculated by a complex algorithm (according to block diagram 2 and 3).

The inclusion of the patient position can in particular help to optimise the control algorithm.

Figure 5:
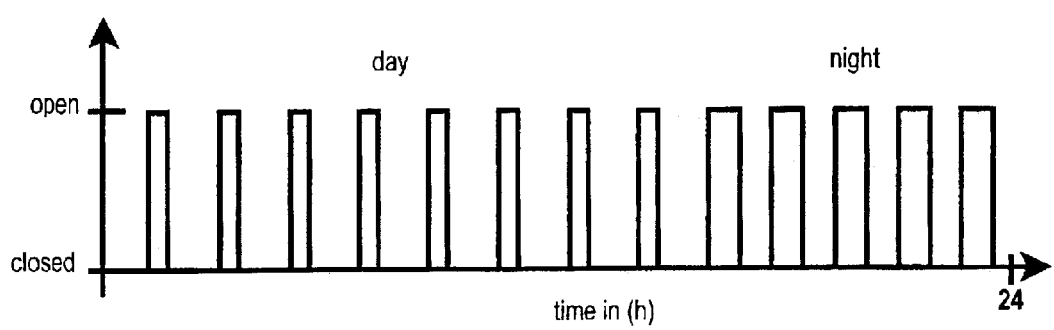

FIG. 5 shows an example of a conceivable control input. The inputs for the switch position may vary depending on the patient and time of day. For example during a reliable lying phase in the night the valve may remain opened for a long time, while during the day the switch may be opened possibly only once an hour for 30 seconds or a few minutes. The signal of the position sensor can shorten or lengthen the opening time. The control signal is transmitted to the implant through the skin. The detection of state data in the implant can be retrieved when needed.

Other embodiments for a switch of this type can be produced as a moved diaphragm. The generation of the movement can take place via moved conductors in the magnetic field as well as via the force, which is exerted on magnets in the magnetic field which is applied for adjustment. Further possibilities for adjustment consist in piezoelectric movement generation or by the control of bimetals.

It will be understood that the above description of the present invention is susceptible to various modification, changes and adaptations.

What is claimed is:

1. A hydrocephalus valve comprising:
   an electrically actuable switching valve, the switching valve comprising a spherical valve body which is configured to rest in a sealing manner on a valve aperture in a closed position and to rest in a recess laterally adjacent to the valve aperture in an open position;
   an electrical actuating system configured to adjust the switching valve between the open position and the closed position,
   wherein the switching valve is stable in the open position and in the closed position when the electrical actuating system is not activated, such that no energy is required to maintain the closed and open positions.

2. A valve according to claim 1, wherein the actuating system comprises a slide which displaces the valve body, on the one hand, and the valve aperture and the recess on the other hand, relative to one another.

3. A valve according to claim 2, wherein a control system actuating the switching valve is provided, the control system being formed as a time control system.

4. A valve according to claim 3, wherein the time control system is programmable.

5. A valve according to claim 1, wherein the actuating system comprises an electromagnetic drive.

6. A valve according to claim 1, wherein the actuating system comprises a piezoelectric drive.

7. A valve according to claim 1, wherein the actuating system comprises a current-carrying bimetal.

8. A valve according to claim 1, wherein a control system actuating the switching valve is provided, the control system being formed as a time control system.

9. A valve according to claim 8, wherein the time control system can be influenced by signals from at least one measuring instrument.

10. A valve according to claim 9, wherein the measuring instrument is a pressure measuring apparatus.

11. A valve according to claim 9, wherein the measuring instrument is a position sensor.

12. A valve according to claim 9, wherein the measuring instrument determines muscle potentials.

13. A valve according to claim 9, wherein the measuring instrument determines brain current potentials.

14. A valve according to claim 8, wherein the time control system is programmable.

15. A valve according to claim 8, wherein a data memory is associated with the time control system.

16. A valve according to claim 8, wherein the time control system changes the opening behaviour of a closure valve.

17. A valve according to claim 1, wherein a control system actuating the switching valve is provided, the control system being formed as a time control system.

18. A valve according to claim 17, wherein the time control system is programmable.

* * * * *